(12) United States Patent
Senetar et al.

(10) Patent No.: US 11,491,453 B2
(45) Date of Patent: Nov. 8, 2022

(54) PROCESS AND APPARATUS FOR REACTING FEED WITH A FLUIDIZED CATALYST OVER A TEMPERATURE PROFILE

(71) Applicant: UOP LLC, Des Plaines, IL (US)

(72) Inventors: John J. Senetar, Naperville, IL (US); Wolfgang A. Spieker, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 240 days.

(21) Appl. No.: 16/942,240

(22) Filed: Jul. 29, 2020

(65) Prior Publication Data

US 2022/0032250 A1 Feb. 3, 2022

(51) Int. Cl.
| | |
|---|---|
| *C10G 11/08* | (2006.01) |
| *B01J 8/00* | (2006.01) |
| *C07C 11/04* | (2006.01) |
| *C07C 11/06* | (2006.01) |
| *C07C 5/333* | (2006.01) |
| *B01J 8/18* | (2006.01) |

(52) U.S. Cl.
CPC .......... *B01J 8/0025* (2013.01); *B01J 8/008* (2013.01); *B01J 8/1863* (2013.01); *C07C 5/333* (2013.01); *C07C 11/04* (2013.01); *C07C 11/06* (2013.01); *B01J 2208/00752* (2013.01); *B01J 2208/00805* (2013.01); *B01J 2208/00991* (2013.01)

(58) Field of Classification Search
CPC ..... C10G 11/18; C10G 11/182; C10G 11/187; C10G 2300/405; C10G 45/04; C10G 45/06; C10G 45/58; C10G 65/04; C07C 11/04; C07C 5/333; C07C 11/06; C07C 5/3335; C07C 5/3332; C07C 5/3337; C07C 5/48; C07C 11/08
See application file for complete search history.

(56) References Cited

U.S. PATENT DOCUMENTS

| | | | |
|---|---|---|---|
| 6,558,531 B2 | 5/2003 | Steffens | |
| 8,753,502 B1 | 6/2014 | Sexton | |
| 9,266,103 B1 | 2/2016 | Davydov | |
| 9,376,633 B2 * | 6/2016 | Palmas | ................ C10G 11/18 |
| 9,597,652 B1 | 3/2017 | Pretz | |
| 9,889,418 B2 | 2/2018 | Pretz | |
| 10,227,271 B2 | 3/2019 | Pretz | |
| 2020/0055015 A1 * | 2/2020 | Pretz | ..................... C10G 11/18 |

* cited by examiner

*Primary Examiner* — Sharon Pregler
(74) *Attorney, Agent, or Firm* — Paschall & Associates, LLC; James C. Paschall

(57) ABSTRACT

A fluidized catalytic reactor utilizes an ascending temperature profile. The apparatus and process deliver cooler spent catalyst to a first catalyst distributor and a hotter regenerated catalyst to a second catalyst distributor that are spaced apart from each other. The reactant stream first encounters the first stream of catalyst and then encounters the second stream of catalyst. The process and apparatus stage the addition of hot catalyst to the reactant stream. The process and apparatus may be particularly advantageous in an endothermic reaction because the hotter catalyst will encounter reactants that have cooled due to the progression of endothermic reactions.

12 Claims, 2 Drawing Sheets

PROCESS AND APPARATUS FOR REACTING FEED WITH A FLUIDIZED CATALYST OVER A TEMPERATURE PROFILE

FIELD

The field is the reaction of feed with fluid catalyst. The field may particularly relate to reacting a paraffin feed with a fluid dehydrogenation catalyst.

BACKGROUND

Light olefin production is vital to the production of sufficient plastics to meet worldwide demand. Paraffin dehydrogenation (PDH) is a process in which light paraffins such as ethane and propane can be dehydrogenated to make ethylene and propylene, respectively. Dehydrogenation is an endothermic reaction which requires external heat to drive the reaction to completion. Fluid catalytic cracking (FCC) is another endothermic process which produces substantial ethylene and propylene.

Dehydrogenation catalyst may incorporate a dehydrogenation metal with a molecular sieve or an amorphous material. The catalyst must be sufficiently robust and appropriately sized to be able to resist the attrition expected in a fluidized system. FCC catalyst is typically a Y zeolite with an optional MFI zeolite to boost propylene production.

In PDH and FCC reactions with fluidized catalyst, coke can deposit on the catalyst while catalyzing the reaction. The catalyst may be regenerated in a catalyst regenerator by combusting coke from the catalyst in the presence of oxygen. The hot regenerated catalyst may then be transferred back to the reactor to catalyze the reaction. If insufficient heat is provided to drive the endothermic reaction, olefin production can suffer.

The catalytic reactions are more selective to the desired products such as propylene than the thermal cracking reactions. Care must be taken to maximize catalytic reactions over thermal cracking reactions.

There is a need, therefore, for improved methods of contacting feed with catalyst in a fluid catalytic reaction process.

BRIEF SUMMARY

A fluidized catalytic reactor utilizes an ascending temperature profile. The apparatus and process deliver cooler spent catalyst to a first catalyst inlet and a hotter regenerated catalyst to a second catalyst inlet that are spaced apart from each other. The reactant stream first encounters the first stream of catalyst and subsequently encounters the second stream of catalyst. The process and apparatus stage the distribution of hot catalyst to the reactant stream. The process and apparatus may be particularly advantageous in an endothermic reaction because the hotter catalyst will encounter reactants that have cooled due to the progression of endothermic reactions.

DEFINITIONS

Figure 1:
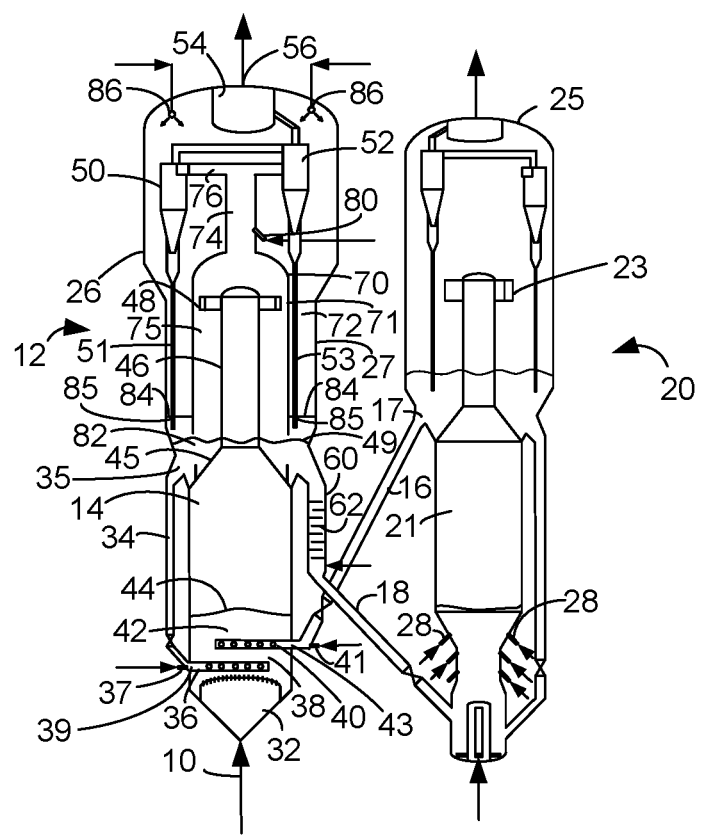
FIG. 1 is a schematic drawing of a process and apparatus of the present disclosure.

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, the term "predominant" or "predominate" means greater than 50%, suitably greater than 75% and preferably greater than 90%.

DETAILED DESCRIPTION

We have discovered a process and apparatus for providing a reactor with a varying temperature profile. In fluid catalytic reaction kinetics, reactions will be marshalled toward greater selectivity to desired products by taking care to ensure that reactants are not exposed to extremely high temperatures. In fluid catalytic endothermic reactions, hot catalyst supplies heat of reaction as well as catalyzing conversion to desired products. Catalyst is typically heated in the regenerator in the process of combusting coke from the catalyst. The catalyst must carry sufficient enthalpy to the reactor to supply heat of reaction for all of the reactants in the feed. Providing catalyst sufficiently hot to drive endothermic conversion of all of the feed distributed to the reactor while avoiding thermal cracking can be a challenge.

We have discovered a way to balance these two competing objectives by establishing a reaction zone with an ascending temperature profile. A hot catalyst is delivered to the reactor and contacted with the feed to initiate catalytic conversion. The feed and catalyst move toward another section of the reactor to which a hotter catalyst is delivered and distributed to the partially converted feed. The ascending temperature profile avoids exposing the feed stream to excessively hot catalyst which could promote nonselective thermal cracking. However, the portions of the feed that have not undergone conversion and have begun to cool due to the endothermicity of the reaction will then be exposed to the hotter catalyst to increase the temperature of the cooled feed and provide sufficient heat to drive the reaction to increase production of the desired products. The disclosed process and apparatus minimize or balance the time in which feed is exposed to hot catalyst.

The teachings herein may be applicable to any process that requires catalyst to be regenerated to provide heat to drive an endothermic catalytic reaction. Paraffin dehydrogenation (PDH) and fluid catalytic cracking (FCC) are examples of such processes. FCC catalyst is used to crack larger hydrocarbon molecules to smaller hydrocarbon molecules at around atmospheric pressure and about 427° C.

(800° F.) to 538° C. (1000° F.) and a catalyst to oil ratio of about 5 to about 30. PDH catalyst is used in a dehydrogenation reaction process to catalyze the dehydrogenation of paraffins, such as ethane, propane, iso-butane, and n-butane, to olefins, such as ethylene, propylene, isobutene and n-butenes, respectively. The PDH process will be described exemplarily to illustrate the disclosed apparatus and process.

The conditions in the dehydrogenation reactor may include a temperature of about 500 to about 800° C., a pressure of about 40 to about 310 kPa and a catalyst to oil ratio of about 5 to about 100. The dehydrogenation reaction may be conducted in a fluidized manner such that gas, which may comprise the reactant paraffins with or without a fluidizing inert gas, is distributed to the reactor in a way that lifts the dehydrogenation catalyst in the reactor vessel while catalyzing the dehydrogenation of paraffins. During the catalytic dehydrogenation reaction, coke is deposited on the dehydrogenation catalyst leading to reduction of the activity of the catalyst. The dehydrogenation catalyst must then be regenerated.

An exemplary PDH reactor 12 is shown in FIG. 1. The PDH reactor 12 may comprise two chambers, a reaction chamber 14 and a separation chamber 26. A feed line 10 may deliver a reactant stream of feed to the reactor 12. The reactant stream may predominantly comprise propane or butane, but other paraffins such as ethane may be present in the reactant stream in conjunction with or to the exclusion of other paraffins. Any feed distributor can distribute the reactant stream to the reactor 12. A domed reactant distributor 32 may be utilized in the reaction chamber 14 of the reactor 12. The domed reactant distributor 32 receives a gaseous reactant stream and distributes the reactant stream through nozzles in the top dome of the domed reactant distributor 32 to distribute the reactant stream across the entire cross section of the reaction chamber 14. It is envisioned that other fluidizing gases may be used to also promote fluidization in the reaction chamber 14. In an embodiment, the distributed reactant stream ascends in the reaction chamber 14 and the reactor 12.

A recycle catalyst pipe 34 has an inlet 35 located in the separation chamber 26 and an outlet comprising a first catalyst inlet 39 which in an embodiment may be connected to a first catalyst distributor 36. The recycle catalyst pipe 34 delivers a first stream of recycled spent catalyst that has not undergone regeneration from the separation chamber 26 through the outlet and the first catalyst inlet 39 to the first section 38 of the reaction chamber 14 in an embodiment through the first catalyst distributor 36. The first catalyst inlet 39 and/or the first catalyst distributor 36 provides spent catalyst to a first section 38 of the reaction chamber 14. The recycled spent catalyst is fed to the reactor 12 through the first catalyst inlet 39 which is the outlet of the recycle catalyst pipe 34. The first catalyst inlet 39 and/or the first catalyst distributor 36 may be contained in the first reaction chamber 14.

The first catalyst distributor 36 can comprise a central pipe with pipes extending from the central pipe in varying angles to spread spent catalyst horizontally over the entire cross section of the reaction chamber 26. A gas assist which may comprise reactant gas or inert gas such a steam may be employed to compel the catalyst out the pipes of the first spent catalyst distributor 36. The gas assist may be delivered from a line through a nozzle 37 in an inlet to the first catalyst distributor 36. The recycled spent catalyst has been in contact with the reactant stream and not been subjected to regeneration. Thus, the recycled spent catalyst has a reduced average temperature resulting from the endothermicity of the reaction. However, the recycled spent catalyst still possesses sufficient enthalpy to catalyze and drive conversion of the reactant stream distributed by the reactant distributor 32. The average temperature of the first stream of catalyst may be about 500 to about 800° C. Consequently, the temperature of the first reaction section 38 may be about 450 to about 750° C.

In the first reaction section 38 the fresh reactant stream is contacted with the first stream of catalyst and the reactant paraffins begin undergoing conversion to olefins, typically propane to propylene. The endothermic dehydrogenation reaction withdraws heat from the mix of the first catalyst stream and the reactant stream while the catalyst and reactants are rising in the reactor impelled by the reactant stream continually entering the reactor through the reactant distributor 32.

To supply additional heat and catalyst to the reaction chamber 14, a second catalyst inlet 43 delivers a second catalyst stream to the reactor 12, in an embodiment through a second catalyst distributor 40. A regenerated catalyst pipe 16 has an inlet 17 located in a regenerator 20 and an outlet connected to the second catalyst inlet 43 and/or the second catalyst distributor 40. The regenerated catalyst pipe 16 delivers a second stream of regenerated catalyst from the regenerator 20 through the outlet to the second catalyst inlet 43 and/or the second catalyst distributor 40. The second catalyst inlet 43 and/or the second regenerated catalyst distributor 40 is contained in and provides hot regenerated catalyst to a second section 42 of the reaction chamber 14. The reactant stream is contacted with the second catalyst stream after contacting the reactant stream with the first catalyst stream. Moreover, the second catalyst stream has a higher temperature than the first catalyst stream. The second regenerated catalyst distributor 40 can comprise a central pipe with pipes extending from the central pipe in varying angles to spread regenerated catalyst horizontally over the entire cross section of the reaction chamber 14. A gas assist which may comprise reactant gas or inert gas such a steam may be employed to compel the catalyst out the pipes of the second regenerated catalyst distributor 40. The gas assist may be delivered from a line through a nozzle 41 in an inlet to the second catalyst distributor 40. The regenerated catalyst has just undergone combustive regeneration and has a very hot average temperature and is active since coke deposits have been combusted from its surface. Hence in the second section 42 of the reaction chamber 14, the reactant stream is provided with additional enthalpy and catalyst to catalytically convert paraffins to olefins, typically propane to propylene. The average temperature of the second stream of catalyst may be about 500 to about 900° C. Consequently, the temperature of the second reaction section 42 may be about 400 to about 800° C. The first catalyst inlet 39 and/or the first catalyst distributor 36 is closer to the reactant distributor 32 than the second catalyst inlet 43 and/or the second catalyst distributor 40. The second catalyst inlet 39 may be spaced apart and may be above the first catalyst inlet 39. The second catalyst distributor 40 may be spaced apart and may be above the first catalyst distributor 36.

In the second reaction section 42 the reactant stream is contacted with the second stream of catalyst and the first stream of catalyst which mix together in the second reaction section, and the reactant paraffins undergo conversion to olefins, typically propane to propylene. The reactant stream and the first stream of catalyst and the second stream of catalyst rise in the reaction chamber 14 of the reactor 12 impelled by the reactant stream continually entering the reactor through the reactant distributor 32. At the interface 44, the fluid dynamics transition from a dense phase of catalyst below the transition to a fast-fluidized flow regime. The catalyst density in the dense phase of catalyst is at least 200 kg/m³ (12.5 lb/ft³); whereas the catalyst density in the fast-fluidized flow regime is at least 100 kg/m³ (6.3 lb/ft). The superficial velocity of the reactant stream and the first stream of catalyst and the second stream of catalyst in the reaction chamber 14 will typically be at least about 0.9 m/s (3 ft/s), suitably at least about 1.1 m/s (3.5 ft/s), preferably at least 1.4 m/s (4.5 ft/s), to about 2.1 m/s (7 ft/s) to provide the fast-fluidized flow regime. Reactant gas and catalyst ascend in a fast-fluidized flow regime in which catalyst may slip relative to the gas and the gas can take indirect upward trajectories.

The dehydrogenation catalyst may be of any of a variety of catalysts suitable for a fluidized dehydrogenation unit. The dehydrogenation catalyst selected should minimize cracking reactions and favor dehydrogenation reactions. Suitable catalysts for use herein include amorphous material or molecular sieves which may be dispersed in a porous inorganic carrier material such as silica, aluminum, zirconium, or clay. An exemplary embodiment of a catalyst includes crystalline silica-alumina or silica-alumina-phosphate as the primary active component, a matrix, a binder, and a filler.

The matrix component may include amorphous alumina or silica, and the binder and filler provide physical strength and integrity. Silica sol or alumina sol may be used as the binder and kaolin clay may be used as the filler. The catalyst particles may have a nominal diameter of about 20 to about 150 micrometers with the average diameter of about 70 to about 90 micrometers.

The dehydrogenation catalyst may support a dehydrogenation metal. The dehydrogenation metal may be a one or a combination of transition metals. A noble metal may be a preferred dehydrogenation metal; however, a IIB or a IIIB metal may be a suitable dehydrogenation metal alone or in combination with other dehydrogenation metals. Iron, tungsten, gallium, copper, zinc or zirconium alone or in combination with each other or a noble metal may be suitable dehydrogenation metals. Combustion promoters may be utilized in addition to the catalyst. Metals may be incorporated into the lattice structure of the molecular sieve.

The acid function of the catalyst should be minimized to prevent cracking and favor dehydrogenation. Alkali metals and alkaline earth metals may be also be included in the catalyst to attenuate the acidity of the catalyst. Rare earth metals may be included in the catalyst to control the activity of the catalyst. Concentrations of 0.05 to 10 wt % metals may be incorporated into the catalyst. In the case of the noble metals, such as platinum, it is preferred to use about 0.05 to about 2 wt % noble metal.

The reactant stream lifts the first stream of catalyst mixed with the second stream of catalyst upwardly in the reaction chamber while paraffins convert to olefins in the presence of the dehydrogenation catalyst which gradually becomes spent catalyst attributed to the agglomeration of coke deposits on the catalyst. A fluidizing inert gas may be distributed to the reaction chamber to assist in lifting the mixture of catalyst and reactants upwardly in the reaction chamber 14. The reactant gases convert to product gases while ascending in the reaction chamber 14. The blend of gases and catalyst ascend from the reaction chamber 14 through a frustoconical transition section 45 into a transport riser 46 which has a smaller diameter than the diameter 40 of the combustion chamber 20. A blend of gases and catalyst accelerate in the narrower transport riser 46 and are discharged from a primary catalyst separator 48 into the separation chamber 26. The primary catalyst separator 48 may be a riser termination device that utilizes horizontal, centripetal acceleration to separate spent catalyst from product gas. Arcuate ducts of the primary catalyst separator 48 direct the mixture of product gas and catalyst to exit from the riser 46 in a typically horizontally angular direction to centripetally accelerate causing the denser catalyst to gravitate outwardly. The catalyst loses angular momentum and falls into a lower catalyst bed 49 depicted with an upper interphase. The lighter gases ascend in the separation chamber 26 and enter into cyclones 50, 52. The cyclones 50, 52 may comprise first and second cyclonic stages of separation to further remove catalyst from product gases. The product gas is ducted to a plenum 54 from which it is discharged from the reactor 12 through a product outlet 56 in a product line. The first catalyst inlet 39 and the second catalyst inlet 43 are closer to the reactant distributor 32 than to the product outlet 56. The primary catalyst separator 48 is located closer to the first catalyst inlet 39 and the second catalyst inlet 43 than the product outlet 56. In an embodiment, the first catalyst distributor 36 and the second catalyst distributor 40 are closer to the reactant distributor 32 than to the product outlet 56. Additionally, the primary catalyst separator 48 is located closer to the first catalyst distributor 36 and the second catalyst distributor 40 than the product outlet 56. The superficial gas velocity in the transport riser 46 will be about 12 m/s (40 ft/s) to about 20 m/s (70 ft/s) and have a density of about 64 kg/m³ (4 lb/ft³) to about 160 kg/m³ (10 lb/ft³), constituting a dilute catalyst phase.

Catalyst separated from the product gas by the primary catalyst separator 48 drops into a dense catalyst bed 49. In an aspect, primary cyclones 50 may collect product gas from the separation chamber 26 and transport the product gas separated from catalyst to a secondary cyclone 52 to further separate catalyst from the product gas before directing secondarily purified product gas to the plenum 54. Catalyst separated from product gas in the cyclones 50, 52 is dispensed by dip legs into the dense catalyst bed 49. At this point, the separated catalyst in the separation chamber 26 is considered spent catalyst because deposits of coke are agglomerated thereon. A regeneration portion of the spent catalyst collected in the dense bed 49 in the separation chamber 26 is transported in a spent catalyst pipe 18 to a catalyst regenerator 20 to have coke burned from the catalyst to regenerate and heat the dehydrogenation catalyst. A vertical section of the spent catalyst pipe 18 may comprise a stripping section 60. A stripping gas such a steam or another inert gas may be fed into a lower end of the stripping section 60 to strip hydrocarbons from the spent catalyst entering the stripping section 60. Baffles may also be provided in the stripping section 60 to cause the spent catalyst to wend laterally in the stripping section to expose more catalyst particles to upwardly flowing stripping gas.

A recycle portion of the spent catalyst collected in the dense bed 49 of the separation chamber 26 enters the recycle catalyst pipe 34 through the inlet 35. The recycle portion of the spent catalyst is recycled in the recycle catalyst pipe 34 back to the first catalyst inlet 39 and/or the first catalyst distributor 36 in the reaction chamber 14 of the reactor 12 as the first catalyst stream. The recycle portion of the spent catalyst is not regenerated before it returns to the reaction chamber 14.

The separation chamber 26 may include a disengagement can 70 that surrounds the upper end of the riser 46 and the primary separator 48. A vertical wall 71 of the disengagement can 70 is spaced apart from a shell 27 of the separation chamber to define an annulus 72. Dip legs of the cyclones 50 and 52 may be located in the annulus 72. The disengagement can 70 serves to limit travel of the product gas exiting the primary separator 48, so as to reduce its time in the reactor 12, thereby mitigating unselective cracking reactions to undesired products. The top of the disengagement can 70 may be hemispherical and feed a gas recovery conduit 74 that transports product gases to ducts 76 that are directly ducted or connected to the primary cyclones 50. The direct ducting from the disengagement can 70 to the primary cyclones 50 also prevents product gas from getting loose in the larger volume of the reactor vessel where excessive residence time may occur to permit unselective cracking. Windows in the lower section of the wall 71 of the disengagement can 70 permit catalyst in the disengagement can to enter into the recycle catalyst pipe 34 or the regeneration pipe 18. A quench fluid such as condensed product liquid or even cool catalyst may be injected into the product gases through a quench nozzle 80 to cool the product gases to below cracking temperature to limit unselective cracking. Quench fluid is advantageously injected into the gas recovery conduit 74 which directs the separated product gas to a narrowed location. The gas recovery conduit 74 is in downstream communication with primary catalyst separator 48 which separates the predominance of the spent catalyst from the product gases. The spent catalyst bypasses quenching to retain heat in the catalyst. The product gases separated from the predominance of the catalyst subjects a reduced mass of material to quenching thereby requiring less quench fluid to achieve sufficient cooling to reduce the temperature of product gas to below cracking temperature.

The stripped, spent dehydrogenation catalyst is transported by the spent catalyst pipe 18 to the regenerator 20 to combust the coke on the spent catalyst and regenerate the spent catalyst into regenerated catalyst. The catalyst regenerator 20 includes a combustion chamber 21 and a catalyst separator 23 which separates regenerated catalyst from flue gas generated in the combustion chamber 21 as they are discharged from the catalyst separator 23. An oxygen supply gas is provided to the combustion chamber 21 which lifts the spent catalyst in the combustion chamber 21 through the catalyst separator 23 and into a separation chamber 25. The coke is burned off the spent catalyst by contact with the oxygen supply gas at regeneration conditions. In an exemplary embodiment, air is used as the oxygen supply gas, because air is readily available and provides sufficient oxygen for combustion. About 10 to about 15 kg of air are required per kg of coke burned off of the spent catalyst. Exemplary regeneration conditions include a temperature from about 500° C. (900° F.) to about 900° C. (1700° F.) and a pressure of about 103 kPa (abs) (15 psia) to about 450 kPa (abs) (70 psia) in the regenerator 20. Hydrocarbon fuel may be added to the regenerator 20 such as through nozzles 28 to boost the heat generated in the regenerator to drive the reaction in the reactor 12.

Regenerated catalyst is returned to the reactor 12 in the regenerated catalyst pipe 16. The regenerated catalyst pipe 16 has an inlet 17 connected to the regenerator 20 in the separation chamber 25 through which regenerated catalyst from the regenerator is transported to the second catalyst distributor 40 in the reactor 12 as the hotter second stream of catalyst. The regenerated catalyst is fed to the reactor 12 through the second catalyst inlet 43 which is the outlet of the regenerated catalyst pipe 16. The regenerated catalyst pipe 16 is connected to the second catalyst inlet 43 which can deliver the regenerated catalyst to the reactor 12 without means of a distributor.

Figure 2:
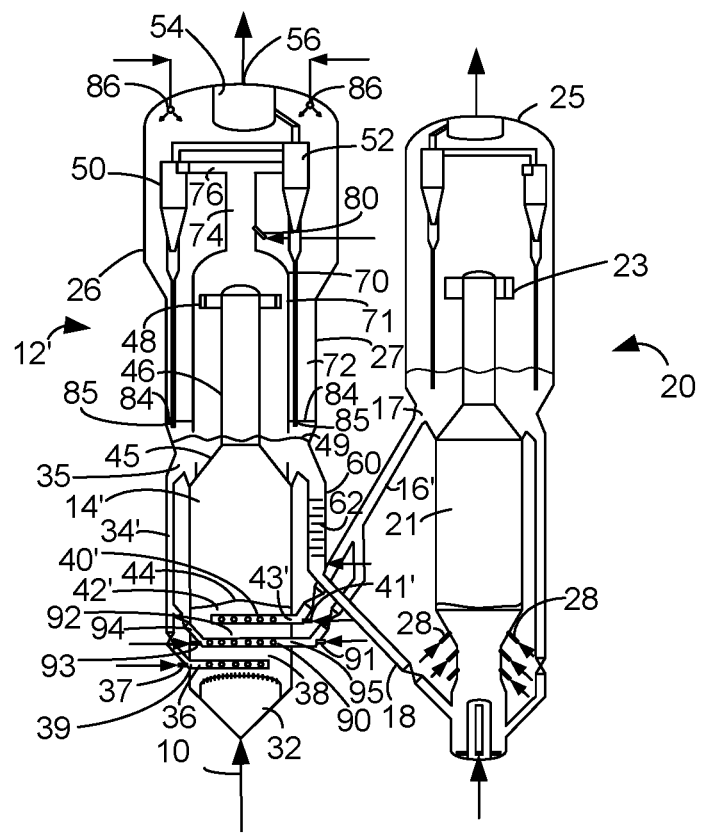
FIG. 2 is a schematic drawing of a process and apparatus of an alternative embodiment of the present disclosure.

FIG. 2 shows an embodiment of an alternative reactor 12' which utilizes three reaction sections and three reactant distributors in the reaction chamber 14' instead of two as in the embodiment of FIG. 1. Elements in FIG. 2 with the same configuration as in FIG. 1 will have the same reference numeral as in FIG. 1. Elements in FIG. 2 which have a different configuration as the corresponding element in FIG. 1 will have the same reference numeral but designated with a prime symbol ('). The configuration and operation of the embodiment of FIG. 2 is essentially the same as in FIG. 1 with the following exceptions.

In between the first catalyst inlet 39 and/or the first catalyst distributor 36 and the second catalyst inlet 43' and/or the second catalyst distributor 40' in the reaction chamber 14' is a third catalyst inlet 94 and a fourth catalyst inlet 95. In an embodiment, the third catalyst inlet 94 and the fourth catalyst inlet 95 feed a third catalyst distributor 90. The third catalyst inlet 94 and/or the third catalyst distributor 90 receives recycled spent catalyst from a branch of the recycle conduit 34'. The fourth catalyst inlet 95 and/or the third catalyst distributor 90 receives regenerated catalyst from the regenerator through a branch of a regenerated catalyst pipe 16'. The two catalyst streams may be mixed in the third catalyst distributor 90 or between the third catalyst inlet 94 and the fourth catalyst inlet 95 to provide a third stream of catalyst, in an embodiment, from the third catalyst distributor 90 at a temperature intermediate to the temperature of the first stream of catalyst from the first catalyst inlet 39 and/or the first catalyst distributor 36 and the second stream of catalyst from the second catalyst inlet 43' or the first second catalyst distributor 40'. The second catalyst inlet 43' and/or the second catalyst distributor 40' is located at a higher elevation than in FIG. 1 to make room for the third catalyst inlet 94, the fourth catalyst inlet 95 and/or the third catalyst distributor 90. The regeneration catalyst pipe 16' has an inlet 17 located in a regenerator 20 and an outlet on a branch connected to the second catalyst inlet 43' and/or the second catalyst distributor 40' and an outlet on a branch connected to the fourth catalyst inlet 95 and/or the third catalyst distributor 90. The regeneration catalyst pipe 16 delivers a second stream of regenerated catalyst from the regenerator 20 through the outlet to the second catalyst inlet 43' and/or the second catalyst distributor 40' and through the outlet to the fourth catalyst inlet 95 and/or the third catalyst distributor 90. The spent catalyst pipe 34' has an inlet 35 located in a the separation chamber 26 and an outlet connected to the first catalyst inlet 39 and/or the first catalyst distributor 36 and an outlet connected to the third catalyst inlet 94 and/or the third catalyst distributor 90 opposite to the fourth catalyst inlet 95 at the outlet of the regenerated catalyst pipe 16'. The spent catalyst pipe 34' delivers recycled spent catalyst from the separation chamber 26 through the outlet on a branch to the first catalyst inlet 39 and/or the first catalyst distributor 36 and through the outlet on a branch to the third catalyst inlet and/or the third catalyst distributor 90. The third catalyst inlet 94 and the fourth catalyst inlet 95 and/or the third catalyst distributor 90 provide a mixture of hot regenerated catalyst and cooler spent catalyst to a third section 92 of the reaction chamber 14' comprising a third catalyst stream. The third catalyst inlet 94 and the fourth catalyst inlet 95 may be spaced apart and may be above the first catalyst distributor 36. The third catalyst distributor 90 may be spaced apart and may be above the first catalyst distributor 36. The reactant stream is contacted with the third catalyst stream after the reactant stream is contacted with the first catalyst stream. Moreover, the third catalyst stream has a higher temperature than the first catalyst stream.

The third catalyst distributor 90 can comprise a central pipe with pipes extending from the central pipe in varying angles to spread mixed spent and regenerated catalyst horizontally over the entire cross section of the reaction chamber 14'. A gas assist which may comprise reactant gas or inert gas such a steam may be employed to compel the catalyst through the third catalyst inlet 94, the fourth catalyst inlet and/or out the pipes of the third catalyst distributor 90. The gas assist may be delivered from a line through a nozzle 91 in the fourth catalyst inlet 95 perhaps to the third catalyst distributor 90 and through a nozzle 93 in the third catalyst inlet 94 on an opposite side, perhaps of the third catalyst distributor 90. In the third section 92 of the reaction chamber 14', the reactant stream is provided with additional enthalpy and catalyst to catalytically convert paraffins to olefins, typically propane to propylene. The average temperature of the third stream of catalyst may be between the average temperature of the first stream of catalyst and the average temperature of the second stream of catalyst. Consequently, the temperature of the third reaction section 92 may be between the temperature of the first reaction section 38 and the second reaction section 42'. The third catalyst inlet 94 and the fourth catalyst inlet 95 are closer to the reactant distributor 32 than the second catalyst distributor 40'. The third catalyst distributor 90 is closer to the reactant distributor 32 than the second catalyst distributor 40'. The reactant stream is then contacted with the hottest second stream of catalyst after the reactant stream is contacted with the first stream of catalyst and the third stream of catalyst. Employment of the third catalyst distributor extends the temperature profile of the catalyst distributed to the reaction chamber 14' over a greater height of the reactor 12'.

The embodiments herein provide a process and apparatus for contacting a reactant stream with fluidized catalyst utilizing an ascending temperature profile.

Specific Embodiments

While the following is described in conjunction with specific embodiments, it will be understood that this description is intended to illustrate and not limit the scope of the preceding description and the appended claims.

A first embodiment of the invention is a process for contacting a reactant stream with catalyst comprising feeding a reactant stream to a reactor; contacting the reactant stream with a first catalyst stream to produce product gases; contacting the reactant stream with a second catalyst stream to produce product gases after contacting the reactant stream with the first catalyst stream, the second catalyst stream having a higher temperature than the first catalyst stream; separating the first catalyst stream and the second catalyst stream from product gases; and discharging the product gases from the reactor. An embodiment of the invention is one, any or all of prior embodiments in this paragraph up through the first embodiment in this paragraph wherein the first catalyst stream and the second catalyst stream separated from the product gases comprise spent catalyst and further comprising regenerating a portion of the spent catalyst to provide the second catalyst stream. An embodiment of the invention is one, any or all of prior embodiments in this paragraph up through the first embodiment in this paragraph further comprising mixing a regenerated catalyst stream with another portion of the spent catalyst to provide a third catalyst stream and the second catalyst stream. An embodiment of the invention is one, any or all of prior embodiments in this paragraph up through the first embodiment in this paragraph wherein the first catalyst stream and the second catalyst stream separated from the product gases comprise spent catalyst and further comprising recycling a portion of the spent catalyst without regeneration to provide the first catalyst stream. An embodiment of the invention is one, any or all of prior embodiments in this paragraph up through the first embodiment in this paragraph further comprising mixing the first catalyst stream and the second catalyst stream in the reactor. An embodiment of the invention is one, any or all of prior embodiments in this paragraph up through the first embodiment in this paragraph further comprising compelling the reactant stream and the first catalyst stream and the second catalyst stream to flow upwardly in the reactor. An embodiment of the invention is one, any or all of prior embodiments in this paragraph up through the first embodiment in this paragraph further comprising contacting the reactant stream with the first catalyst stream and the second catalyst stream in a first chamber and the separating the first catalyst stream and the second catalyst stream from the product gases in a second chamber to provide spent catalyst. An embodiment of the invention is one, any or all of prior embodiments in this paragraph up through the first embodiment in this paragraph further comprising regenerating a portion of the spent catalyst from the second chamber to provide the second catalyst stream and recycling another portion of the spent catalyst from the second chamber to provide the first catalyst stream.

A second embodiment of the invention is a process for contacting a paraffin reactant stream with dehydrogenation catalyst comprising feeding the paraffin reactant stream to a reactor; contacting the paraffin reactant stream with a first dehydrogenation catalyst stream to produce olefin product gases; contacting the paraffin reactant stream with a second dehydrogenation catalyst stream to produce olefin product gases after contacting the reactant paraffin stream with the first dehydrogenation catalyst stream, the second dehydrogenation catalyst stream having a higher temperature than the first dehydrogenation catalyst stream; separating the first dehydrogenation catalyst stream and the second dehydrogenation catalyst stream from the olefin product gases; and discharging the olefin product gases from the reactor. An embodiment of the invention is one, any or all of prior embodiments in this paragraph up through the second embodiment in this paragraph wherein the first dehydrogenation catalyst stream and the second dehydrogenation catalyst stream separated from the olefin product gases comprise spent dehydrogenation catalyst and further comprising regenerating a portion of the spent dehydrogenation catalyst to provide the second dehydrogenation catalyst stream and recycling another portion of the spent dehydrogenation catalyst to provide the first dehydrogenation catalyst stream. An embodiment of the invention is one, any or all of prior embodiments in this paragraph up through the second embodiment in this paragraph further comprising contacting the paraffin reactant stream with the first dehydrogenation catalyst stream and the second dehydrogenation catalyst stream in a first chamber and separating the first dehydrogenation catalyst stream and the second dehydrogenation catalyst stream from the olefin product gases in a second chamber to provide spent dehydrogenation catalyst. An embodiment of the invention is one, any or all of prior embodiments in this paragraph up through the second embodiment in this paragraph further comprising compelling the paraffin reactant stream and the first dehydrogenation catalyst stream and the second dehydrogenation catalyst stream to flow upwardly in the reactor.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for contacting a reactant stream with catalyst comprising:
   feeding a reactant stream to a reactor;
   contacting said reactant stream with a first catalyst stream to produce product gases;
   contacting said reactant stream with a second catalyst stream to produce product gases after contacting said reactant stream with said first catalyst stream, said second catalyst stream having a higher temperature than said first catalyst stream;
   separating said first catalyst stream and said second catalyst stream from product gases; and
   discharging said product gases from said reactor.

2. The process of claim 1 wherein said first catalyst stream and said second catalyst stream separated from said product gases comprise spent catalyst and further comprising regenerating a portion of said spent catalyst to provide said second catalyst stream.

3. The process of claim 2 further comprising mixing a regenerated catalyst stream with another portion of said spent catalyst to provide a third catalyst stream and said second catalyst stream.

4. The process of claim 1 wherein said first catalyst stream and said second catalyst stream separated from said product gases comprise spent catalyst and further comprising recycling a portion of said spent catalyst without regeneration to provide said first catalyst stream.

5. The process of claim 1 further comprising mixing the first catalyst stream and the second catalyst stream in the reactor.

6. The process of claim 1 further comprising compelling the reactant stream and the first catalyst stream and the second catalyst stream to flow upwardly in the reactor.

7. The process of claim 1 further comprising contacting the reactant stream with the first catalyst stream and the second catalyst stream in a first chamber and said separating said first catalyst stream and said second catalyst stream from said product gases in a second chamber to provide spent catalyst.

8. The process of claim 7 further comprising regenerating a portion of said spent catalyst from said second chamber to provide said second catalyst stream and recycling another portion of said spent catalyst from said second chamber to provide said first catalyst stream.

9. A process for contacting a paraffin reactant stream with dehydrogenation catalyst comprising:
   feeding said paraffin reactant stream to a reactor;
   contacting said paraffin reactant stream with a first dehydrogenation catalyst stream to produce olefin product gases;
   contacting said paraffin reactant stream with a second dehydrogenation catalyst stream to produce olefin product gases after contacting said reactant paraffin stream with said first dehydrogenation catalyst stream, said second dehydrogenation catalyst stream having a higher temperature than said first dehydrogenation catalyst stream;
   separating said first dehydrogenation catalyst stream and said second dehydrogenation catalyst stream from said olefin product gases; and
   discharging said olefin product gases from said reactor.

10. The process of claim 9 wherein said first dehydrogenation catalyst stream and said second dehydrogenation catalyst separated from said olefin product gases comprise spent dehydrogenation catalyst and further comprising regenerating a portion of said spent dehydrogenation catalyst to provide said second dehydrogenation catalyst stream and recycling another portion of said spent dehydrogenation catalyst to provide said first dehydrogenation catalyst stream.

11. The process of claim 10 further comprising contacting the paraffin reactant stream with the first dehydrogenation catalyst stream and the second dehydrogenation catalyst stream in a first chamber and separating said first dehydrogenation catalyst stream and said second dehydrogenation catalyst stream from said olefin product gases in a second chamber to provide spent dehydrogenation catalyst.

12. The process of claim 9 further comprising compelling the paraffin reactant stream and the first dehydrogenation catalyst stream and the second dehydrogenation catalyst stream to flow upwardly in the reactor.

* * * * *